(12) United States Patent
Thompson et al.

(10) Patent No.: US 11,525,761 B2
(45) Date of Patent: *Dec. 13, 2022

(54) LIQUID VAPORIZATION DEVICE AND METHOD

(71) Applicant: Mustang Sampling, LLC, Ravenswood, WV (US)

(72) Inventors: Kenneth O. Thompson, Ravenswood, WV (US); Kevin Warner, The Woodlands, TX (US); William C. Paluch, Jersey Village, TX (US)

(73) Assignee: Mustang Sampling, LLC, Ravenswood, WV (US)

( * ) Notice: Subject to any disclaimer, the term of this patent is extended or adjusted under 35 U.S.C. 154(b) by 185 days.

This patent is subject to a terminal disclaimer.

(21) Appl. No.: 17/145,725

(22) Filed: Jan. 11, 2021

(65) Prior Publication Data

US 2021/0140859 A1    May 13, 2021

Related U.S. Application Data

(63) Continuation of application No. 16/749,157, filed on Jan. 22, 2020, now Pat. No. 10,921,225, which is a
(Continued)

(51) Int. Cl.
*G01N 1/44* (2006.01)
*H05B 3/06* (2006.01)
(Continued)

(52) U.S. Cl.
CPC ............... *G01N 1/44* (2013.01); *G01N 33/28* (2013.01); *H05B 1/0297* (2013.01); *H05B 3/06* (2013.01)

(58) Field of Classification Search
CPC ...... G01N 1/10; G01N 1/22; G01N 2001/105; G01N 30/20; G01N 1/2202; G01N 1/2214;
(Continued)

(56) References Cited

U.S. PATENT DOCUMENTS 2,665,239 A   1/1954   Howard et al.
3,053,077 A   11/1962  Tracht
(Continued)

FOREIGN PATENT DOCUMENTS

CN   1090915 A   8/1994
CN   1623063 A   6/2005
(Continued)

OTHER PUBLICATIONS

India Intellectual Property, Patent and Trademark Office International Examination Report for PCT Application No. PCT/US2019/047841, dated Sep. 9, 2021.
(Continued)

*Primary Examiner* — Nimeshkumar D Patel
*Assistant Examiner* — Gedeon M Kidanu
(74) *Attorney, Agent, or Firm* — Cahn & Samuels, LLP

(57) ABSTRACT

A vaporizer device and associated methodology for providing accurate sampling through substantially efficient, complete and uniform single pass vaporization of a liquid sample by avoiding liquid pre-vaporization and downtime attributable to system damage from incomplete vaporization, particularly in the distribution, transportation, and custody transfer of natural gas. The vaporizer device includes at least one input port for receiving a liquid sample, a channel for directing the liquid to a vaporizer core and a heating assembly within the vaporizer core configured to flash vaporize the liquid sample. The vaporized sample can then be passed to an outlet for sample analysis.

16 Claims, 13 Drawing Sheets

Related U.S. Application Data continuation of application No. 16/542,666, filed on Aug. 16, 2019, now Pat. No. 10,613,006.

(60) Provisional application No. 62/735,375, filed on Sep. 24, 2018.

(51) Int. Cl.
*H05B 1/02* (2006.01)
*G01N 33/28* (2006.01)

(58) Field of Classification Search
CPC ...... G01N 1/2226; G01N 1/2247; G01N 1/44; G01N 2001/2238; G01N 2001/2261; G01N 2001/2267; G01N 2030/204; G01N 2030/8886; G01N 30/12; G01N 30/30; G01N 33/22; G01N 33/225; F17C 13/02; F17C 2221/033; F17C 2223/0161; F17C 2223/033; F17C 2223/046; F17C 2225/0123; F17C 2225/0161; F17C 2225/033; F17C 2225/035; F17C 2227/0135; F17C 2227/0302; F17C 2227/0311; F17C 2227/0318; F17C 2227/0332; F17C 2227/0393; F17C 2250/0447; F17C 2250/0456; F17C 2260/024; F17C 2265/05; F17C 2265/061; F17C 2270/0105; F17C 2270/0136; F17C 2270/0171; F17C 6/00; F17C 7/04; F17C 9/00; F17C 9/02; H05B 1/0244; H05B 2203/021
See application file for complete search history.

(56) References Cited

U.S. PATENT DOCUMENTS

| | | | |
|---|---|---|---|
| 3,327,520 A | 6/1967 | Stapp, Jr. | |
| 3,401,565 A * | 9/1968 | Stoll | G01N 30/12 73/864.83 |
| 3,421,336 A | 1/1969 | Lichtenberger et al. | |
| 3,605,808 A * | 9/1971 | Fisher | F16K 15/1823 137/601.19 |
| 3,609,983 A | 10/1971 | Lofredo et al. | |
| 3,661,202 A | 5/1972 | Moore, Jr. | |
| 3,720,092 A | 3/1973 | Reinecke | |
| 3,739,634 A | 6/1973 | Johnson et al. | |
| 3,933,030 A | 1/1976 | Forester et al. | |
| 3,976,450 A | 8/1976 | Marcote et al. | |
| 3,986,846 A | 10/1976 | Bivins, Jr. | |
| 4,007,626 A | 2/1977 | Roof et al. | |
| 4,296,637 A | 10/1981 | Calamur et al. | |
| 4,458,541 A * | 7/1984 | Deming | G01N 30/20 73/864.83 |
| 4,519,213 A | 5/1985 | Brigham et al. | |
| 4,735,259 A | 4/1988 | Vincent | |
| 4,974,453 A | 12/1990 | Hohorst | |
| 5,205,177 A | 4/1993 | DuBrock, Jr. | |
| 5,321,984 A | 6/1994 | Stroupe | |
| 5,363,874 A | 11/1994 | Henszey et al. | |
| 5,390,500 A | 2/1995 | White et al. | |
| 5,505,782 A | 4/1996 | Stauffer | |
| 5,544,276 A | 8/1996 | Loux et al. | |
| 5,596,154 A | 1/1997 | Baughman | |
| 5,836,290 A | 11/1998 | Gilbert | |
| 5,907,107 A | 5/1999 | Welker | |
| 5,918,595 A | 7/1999 | Olsson et al. | |
| 6,042,634 A | 3/2000 | Van Tassel et al. | |
| 6,044,825 A | 4/2000 | Carter et al. | |
| 6,299,767 B1 | 10/2001 | Dourdeville | |
| 6,357,304 B1 | 3/2002 | Mayeaux | |
| 6,382,227 B1 | 5/2002 | Birch et al. | |
| 6,408,895 B1 | 6/2002 | Beam | |
| 6,439,031 B1 | 8/2002 | Pieroni et al. | |
| 6,464,101 B1 | 10/2002 | Siragusa | |
| 6,598,408 B1 | 7/2003 | Nierenberg | |
| 6,701,794 B2 | 3/2004 | Mayeaux | |
| 6,827,046 B2 | 12/2004 | Well | |
| 6,848,502 B2 | 2/2005 | Bishop et al. | |
| 6,904,816 B2 | 6/2005 | Mayeaux | |
| 6,981,850 B1 | 1/2006 | Malthie et al. | |
| 7,004,041 B2 | 2/2006 | Mayeaux | |
| 7,134,318 B2 | 11/2006 | Mayeaux | |
| 7,162,933 B2 | 1/2007 | Thompson et al. | |
| 7,293,600 B2 | 11/2007 | Nierenburg | |
| 7,337,616 B2 | 3/2008 | Meneses et al. | |
| 7,464,724 B2 * | 12/2008 | Carter | B08B 3/02 137/601.19 |
| 7,484,404 B2 | 2/2009 | Thompson et al. | |
| 7,723,700 B2 | 5/2010 | Horsky et al. | |
| 7,882,729 B2 | 2/2011 | Thompson et al. | |
| 8,056,399 B2 | 11/2011 | Thompson et al. | |
| 8,307,843 B2 | 11/2012 | Patterson et al. | |
| 8,347,694 B2 | 1/2013 | Welker et al. | |
| 8,713,995 B2 | 5/2014 | Thompson et al. | |
| 9,057,668 B2 | 6/2015 | Thompson et al. | |
| 9,097,695 B2 | 8/2015 | Kriel et al. | |
| 9,164,016 B2 | 10/2015 | Barere | |
| 9,285,299 B2 | 3/2016 | Thompson et al. | |
| 9,625,431 B2 | 4/2017 | Thompson et al. | |
| 9,877,521 B1 * | 1/2018 | Gillis | A24F 40/42 |
| 10,107,722 B2 * | 10/2018 | Rolston | G01N 1/2202 |
| 10,281,368 B2 | 5/2019 | Thompson et al. | |
| RE47,478 E | 7/2019 | Thompson | |
| 10,436,678 B1 | 10/2019 | St. Amant, III | |
| 10,613,004 B1 | 4/2020 | St. Amant, III | |
| 10,641,687 B1 | 5/2020 | St. Amant, III | |
| 2002/0020209 A1 | 2/2002 | Grob et al. | |
| 2003/0116091 A1 * | 6/2003 | Grant | C23C 16/4486 427/248.1 |
| 2003/0228707 A1 | 12/2003 | Meneses et al. | |
| 2006/0000298 A1 * | 1/2006 | Thompson | G01N 1/2247 73/861.11 |
| 2006/0151495 A1 | 7/2006 | Kabasawa et al. | |
| 2009/0151427 A1 * | 6/2009 | Thompson | H05B 3/44 392/394 |
| 2009/0155642 A1 | 6/2009 | Popham | |
| 2009/0193884 A1 | 8/2009 | Moore et al. | |
| 2010/0012201 A1 | 1/2010 | Welker | |
| 2012/0011919 A1 | 1/2012 | Kriel | |
| 2012/0048881 A1 | 3/2012 | Drube et al. | |
| 2012/0118566 A1 | 5/2012 | Vandor | |
| 2012/0130359 A1 | 5/2012 | Turovskiy | |
| 2012/0180556 A1 | 7/2012 | Webster | |
| 2012/0222422 A1 | 9/2012 | Nunley | |
| 2012/0272715 A1 | 11/2012 | Kriel et al. | |
| 2013/0263680 A1 * | 10/2013 | Barere | G01N 1/44 73/863.12 |
| 2014/0137599 A1 | 5/2014 | Oelfke | |
| 2016/0361452 A1 | 12/2016 | Blackley | |

FOREIGN PATENT DOCUMENTS

| | | |
|---|---|---|
| CN | 103370568 B | 5/2015 |
| EP | 0134690 A2 | 3/1985 |
| EP | 0186618 A2 | 7/1986 |
| WO | 2006/091543 A2 | 8/2006 |
| WO | 2012/145606 A2 | 10/2012 |
| WO | 2014/143712 A2 | 9/2014 |

OTHER PUBLICATIONS

European App. No.: EP 05769462.2, Supplementary European Search Report, dated Apr. 5, 2012.

Energy Information Administration, Office of Oil and Gas, "U.S. LNG Markets and Uses," Jan. 2003.

Zoss, Michelle M. Ph.D., "Introduction to LNG; An Overview on liquefied natural gas (LNG), its properties, the LNG industry, safety considerations", Energy Economics Research at the Bureau of Economic Geology, Center for Energy Economics, Jan. 2003.

(56) References Cited

OTHER PUBLICATIONS

Tarlowski, Janusz, et al., "LNG Import Terminals—Recent Developments," 2005.
United States of America Federal Energy Regulatory Commission, "Notice of Availability of Staff's Responses to Comments on the Consequence Assessment Methods for Incidents Involving Releases from Liquefied Natural Gas Carriers," Jun. 18, 2004.
Energy Information Administration, "U.S. Natural Gas Markets: Mid Term Prospects for Natural Gas Supply", Dec. 2001.
European App. No. EP 06735575, Supplementary European Search Report, dated Aug. 7, 2015.
European Application No. 06735575.0, Opinion, dated Jan. 23, 2020.
United States International PCT App. No. PCT/US 06/05981, ISR/WO dated Sep. 24, 2007.
Doyle, David, et al.,: "Processes and Pump Services in the LNG Industry," Proceedings of the Twenty-Second International Pump Users Symposium, 2005, pp. 179-185.
"White Paper on Liquid Hydrocarbon Drop Out in Natural Gas Infrastructure," NGC+ Liquid Hydrocarbon Dropout Task Group, Feb. 28, 2005.
Technical White Paper "Sample Liquid Petroleum Gas (and other high vapor pressure gas/liquids)", Sentry Equipment Corp, Tec1. 621 Rev. 0.
International Application No. PCT/US2015/015423, Notification of Transmittal of the International Search Report and the Written Opinion of the International Searching Authority, or the Declaration, dated Jun. 25, 2015.
European Patent Office, Application No. 15748549, Extended Search Report, dated Sep. 8, 2017.
Intellectual Property Office of Singapore, Search Report, Application No. 11201606436S, dated Jul. 10, 2017.
Genie GV Vaporizer, "Five times more heat transfer capacity than vaporizing regulators!", 2012.
Stockwell, Peter B. et al, "Mercury Measurements in Fossil Fuels, Particularly Petrochemicals", Jan. 2006, vol. 3, No. 1, Journal of ASTM International.
English Abstract of CN10370568, dated May 27, 2015.
International Search Report & Written Opinion of the International Searching Authority, dated Oct. 18, 2019.
China Office Action dated Mar. 16, 2022, Appl. No. 201980075446. 1.
Machine Translation of China Office Action, dated Mar. 16, 2022.

* cited by examiner

LIQUID VAPORIZATION DEVICE AND METHOD

FIELD OF THE INVENTION

This invention relates generally to a device and method for the efficient vaporization of heterogenous hydrocarbon containing liquids and particularly natural gas liquids such as Natural Gas Liquid (NGL) and cryogenic Liquid Natural Gas (LNG). The invention is particularly useful for uniform flash vaporization of liquid samples, without pre-vaporization, extracted from a source in order to provide uniform sample vapor for accurately determining the constituent components or energy content of the sample.

BACKGROUND OF THE INVENTION

Natural gas is a combustible, gaseous mixture of several different hydrocarbon compounds now often extracted by fracking from underground reservoirs within porous rock. The hydrocarbon constituents of natural gas vary depending on the geographic location of the reservoir and even locally where the composition of gas extracted from a single source can vary. Regardless of any variations, however, the primary component of natural gas is methane, a colorless, odorless, gaseous saturated hydrocarbon. Methane usually accounts for 80% to 95% of any natural gas sample and the balance is composed of varying amounts of ethane, propane, butane, pentane and other hydrocarbon compounds. Some extracted natural gas may contaminated with small amounts of impurities that require detection and removal. Sour gas can comprise trace contaminants such as, Mercury (Hg), Hydrogen sulfide ($H_2S$), Carbonyl sulfide (COS), Mercaptans (RSH), and aromatic compounds including those from the group known as BTEX (Benzene, Toluene, Ethylbenzene and Xylene).

Natural gas is used extensively in residential, commercial and industrial applications. It is the dominant energy used for home heating with well over half of American homes using natural gas. The use of natural gas is also rapidly increasing in electric power generation and as a transportation fuel.

Natural gas is commercially measured by the amount of energy it contains. The common unit of measurement in the United States is the British Thermal Unit (BTU). One BTU is equivalent to the heat needed to raise the temperature of one pound of water by one-degree Fahrenheit at atmospheric pressure. A cubic foot of natural gas has about 1,027 BTU (1083.54 kilojoules (kJ)). Natural gas is normally sold from the wellhead, i.e., the point at which the gas is extracted from the earth, to purchasers in standard volume measurements of thousands of cubic feet (Mcf). However, consumer bills are usually measured in heat content or therms. One therm is a unit of heating equal to 100,000 BTU (105,505.59 kJ).

Three separate and often independent segments of the natural gas industry are involved in delivering natural gas from the wellhead to the consumer. Production companies explore, drill and extract natural gas from the ground; transmission companies operate the pipelines that connect the gas fields to major consuming areas; and distribution companies are the local utilities that deliver natural gas to the customer.

In the United States alone, natural gas is delivered to close to 200 million consumers through a network of underground pipes that extends over a million miles. To produce and deliver this natural gas there are over a quarter-million producing natural gas wells, over one hundred natural gas pipeline companies and more than a thousand local distribution companies (LDCs) that provide gas service to all 50 states.

Pipeline companies transport gas from sellers, such as producers or marketers, to buyers, such as electric utilities, factories and LDCs. LDCs can choose among a variety of sellers of natural gas and customers may choose its LDC supplier. The consumer's LDC, as the owner/operator of the distribution network, delivers the gas to the consumer, but the LDC only charges the consumer for delivery of the gas and the independent supplier bills for the gas. Not only upon extraction form the ground but at each of the stages of custody transfer, energy content analysis provides critical value information to the purchaser.

An important part of the art in gas sample conditioning relates to the process of vaporization of a liquid sample extracted via a probe from a gas pipeline or source. Once the liquid sample is extracted, it is typically communicated from the take-off probe through a corrosion-resistant super alloy, such as stainless-steel tubing, with a relatively small diameter to a sample conditioner for vaporization, pressure regulation, and ultimately to an analyzer, such as a chromatograph, for analysis.

The distance between the liquid probe takeoff and the analyzer often exceeds 30 feet (9.144 meters) and may even exceed 100 feet (30.48 meters). When, as is typical, the extracted liquid sample is vaporized proximate to the probe, the vaporized sample must move physically from the probe at a high pressure, e.g., 2000 psig (13789.51 kPa), to the analyzer while preserving the vapor stage and being subject to substantial pressure reduction to a relatively low-pressure zone, e.g., 10-30 psig (68.9 kPa-206.8 kPa), which is an acceptable pressure for a typical analyzer/chromatograph. During the process, it is important to avoid cooling the vapor to a point near the vapor phase curve to minimize the risk of hydrocarbon dew point dropout in the form of condensation.

If such condensation occurs, then the input to the analyzer/chromatograph is fouled with liquid. Introduction of such liquid invariably compromises the integrity of and damages the chromatographic packing by column bleed, that will, at best, result in generation of false readings from ghost peaks, etc., and at worst, destroy the analyzer. Consequently, introduction of liquids into the chromatographic analyzer results in economic harm, at best, from false readings, and at worst, decreased system operational efficiency attributable to taking the fouled unit off-line either for complete replacement or for restoration to an operationally acceptable condition.

Accordingly, it is important to maintain the integrity of the vaporized liquid sample, without any phase change, for the entire period from flash vaporization to the time of analysis.

Particularly in the case of hydrocarbon vapor analysis, the issue of hydrocarbon dew point dropout in gas sampling has been addressed. Dew point dropout or phase transition of an extracted pipeline sample is prevented by maintaining adequate post-vaporization heating of pressure regulators, gas lines, and other components, with which the sample gas come into contact following vaporization, during communication to a downstream analyzer/chromatograph or vapor sample collection vessel. Maintaining pressure and temperature of the vaporized sample beyond its dew point-phase transition envelope, whether the sample comprises a heterogeneous mixture of components possessing a range of vapor condensation lines or a substantially homogeneous composition with a more predicable phase envelope curve such as LNG, prevents the vapor gas sample from reverting to a liquid.

Natural gas sampling systems, however, are typically located in harsh environments, e.g., where outdoor ambient temperatures can be significantly below the gas dew point temperature and where dangerous explosion-prone gas vapors are often permeating into the surrounding atmosphere. Accordingly, any heating mechanism used must adhere to strict standards in order to generate enough heat to overcome the low ambient temperature while doing so without exposing or releasing the gas samples gases to atmosphere and avoiding safety problems, caused by exposure of vaporized sample gas to electrical wiring, etc.

The American Petroleum Institute (API) has suggested using catalytic heaters to maintain temperature stability of extracted samples to avoid undesirable temperature changes to the gas sample communicated between a source, e.g., pipeline and the analyzer. Catalytic heaters of the type referred to by the API in its Manual of Petroleum Standards call for heating a sample gas stream throughout a selected portion of a system where the heated sample is then introduced into the analyzer at an acceptable pressure. One preferred system for achieving proper system thermal stability employs heat tracing to insure substantially uniform temperature maintenance over the entire length of the vaporized sample pathway during sample communication from take-off to the analyzer. Such performance is achieved with use of a P53 Sample Conditioning System available from Mustang Sampling, LLC of Ravenswood, W. Va. and embodiments disclosed and described in U.S. Pat. No. 7,162,933, the entirety of which is herein incorporated by reference.

Turning to issues associated with vaporization itself, vaporization devices in which a low carbon number hydrocarbon liquid, such as natural gas liquid (NGL) and particularly cryogenic LNG, is vaporized by heating may suffer from development of temperature gradations proximate to a liquid sample entry port. In the case of such temperatures exceeding the heat of vaporization, pre-vaporization of the liquid sample may result. When an extracted liquid sample is subject to partial or complete vaporization proximate to the vaporizer input, but before reaching a heated vaporization chamber, the integrity of the vaporized sample exiting a vaporizer may be compromised by undesirable partitioning of product components (lights, intermediaries, and heavies) separating and entering the vaporizer at different times. Such partitioning or separation will generally lead to faulty energy content and compositional analysis. Further, in the event that the pre-vaporized sample is exposed to subsequent cooling or pressure reduction causing re-condensation during the passage into the vaporization chamber, further undesirable compositional stratification/partitioning may result. Additionally, where pre-vaporization occurs at the vaporizer input, the cooling effect created by the expansion of the liquid to gas can generate exterior icing upstream of the entry port and thereby augment thermal anomalies which further compromise sample uniformity and integrity.

There exists a need for improvement to the presently accepted and commonly used systems and methods of vaporization of extracted natural gas samples for analysis deployable in the field, in distribution systems, and in transportation. It would be desirable to provide an improved vaporizer that ensures accurate sampling through substantially efficient, complete and uniform single pass vaporization of a liquid sample that avoids liquid pre-vaporization and downtime attributable to system damage from incomplete vaporization, particularly in the distribution, transportation, and custody transfer of natural gas.

SUMMARY OF THE INVENTION

It is an object of the invention to provide a device, system and method that do not suffer from at least the problems described previously herein and which can provide a more efficient and reliable vaporizing device for converting LNG or NGL to gaseous vapor.

Yet another object of the invention is to provide a device that delivers better heat distribution while reducing the number of hot spots that lead to the formation of deposits within the device.

It is yet another object of the invention to provide a device that is more compact, easier to adjust, and less susceptible to mechanical failure while also providing for operating efficiencies.

Another object of the invention is to provide a device and method for efficiency vaporizing different types of LNG or NGL samples having different composition profiles.

Yet another object of the invention is to monitor and control the temperature of vapor samples exiting the vaporizer device to prevent damage to the vaporizer itself and/or downstream analyzers.

It is a further object of the invention to provide a device, system and method that can be used to deliver more accurate measurement of BTU values used for custody transfer. Further, to monitor and reduce undesired release from sour gas samples, the device, system and method can also be used to accurately measure trace contaminants such as, mercury (Hg), hydrogen sulfide ($H_2S$), carbonyl sulfide (COS), mercaptans (RSH) and aromatics such as BTEX (Benzene, Toluene, Ethylbenzene and Xylene).

Illustrative, non-limiting embodiments of the present invention may overcome the aforementioned and other disadvantages associated with related art liquid vaporization and measurement systems. Also, the present invention is not necessarily required to overcome the disadvantages described above and an illustrative non-limiting embodiment of the present invention may not overcome any of the problems described above.

To achieve the above and other objects an embodiment in accordance with the invention includes a vaporizer for a hydrocarbon containing liquid, comprising: a generally elongated tubular body having a first segment defining a first end and a second segment defining a second end; a liquid sample port connected to a liquid passage formed integrally in the first segment, where said first liquid port provides for liquid input; a liquid channel disposed generally longitudinally along a central axis of the vaporizer and extending substantially in the direction of elongation of said tubular body, said liquid channel having a first end and a second end, said first end of said liquid channel intersecting with said liquid passage to provide a flow path for liquid from said liquid sample port therethrough along its length; a liquid flow control element disposed in said first segment of said tubular body and configured to intersect the liquid channel; a gap formed in and extending from an exterior surface of the tubular body, the gap defining a generally non-parallel surface directed inwardly toward the liquid channel and disposed along the length of the liquid channel; a vaporizer core internal to and extending from said second end of said tubular body to said second end of said liquid channel; a heating assembly dimensioned for insertion into the vaporizer core and sealingly securable to said tubular body, said heating assembly having a flash vaporizing heating element that vaporizes liquid introduced from said liquid channel; and a vapor discharge outlet port formed in said tubular body in said second segment spaced from said second end of the tubular body and intersecting with said vaporizer core.

BRIEF DESCRIPTION OF THE DRAWINGS

The aspects of the present invention will become more readily apparent by describing in detail illustrative, non-limiting embodiments thereof with reference to the accompanying drawings, in which.

DETAILED DESCRIPTION

Figure 1A:
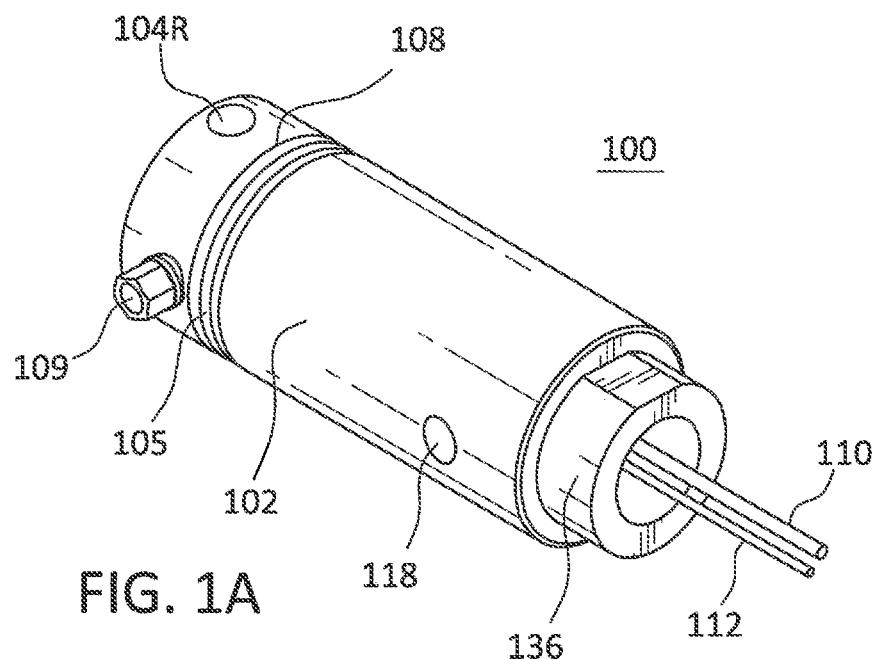
FIG. 1A is a perspective view illustrating a vaporizer device in accordance with an embodiment of the present invention.

Exemplary, non-limiting, embodiments of the present invention are discussed in detail below. While specific configurations and dimensions are discussed to provide a clear understanding, it should be understood that the disclosed dimensions and configurations are provided for illustration purposes only. A person skilled in the relevant art will recognize that, unless otherwise specified, other dimensions and configurations may be used without departing from the spirit and scope of the invention.

As used herein "substantially", "relatively", "generally", "about", and "approximately" are relative modifiers intended to indicate permissible variation from the characteristic so modified. They are not intended to be limited to the absolute value or characteristic which it modifies but rather approaching or approximating such a physical or functional characteristic.

In the detailed description, references to "one embodiment", "an embodiment", or "in embodiments" mean that the feature being referred to is included in at least one embodiment of the invention. Moreover, separate references to "one embodiment", "an embodiment", or "in embodiments" do not necessarily refer to the same embodiment; however, neither are such embodiments mutually exclusive, unless so stated, and except as will be readily apparent to those skilled in the art. Thus, the invention can include any variety of combinations and/or integrations of the embodiments described herein.

The terminology used herein is for the purpose of describing particular embodiments only and is not intended to be limiting of the invention. As used herein, the singular forms, "a", "an" and "the" are intended to include the plural forms as well, unless the context clearly indicates otherwise. It will be further understood that the root terms "include" and/or "have", when used in this specification, specify the presence of stated features, integers, steps, operations, elements, and/or components, but do not preclude the presence or addition of at least one other feature, integer, step, operation, element, component, and/or groups thereof.

It will be appreciated that as used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus.

It will also be appreciated that as used herein, any reference to a range of values is intended to encompass every value within that range, including the endpoints of said ranges, unless expressly stated to the contrary.

As used herein "gas" means any type of gaseous, vaporizable hydrocarbon containing liquid matter including natural gas liquids, and liquified natural gas, gas mixtures thereof, and equivalents.

As used herein "connected" includes physical, whether direct or indirect, permanently affixed or adjustably mounted. Thus, unless specified, "connected" is intended to embrace any operationally functional connection.

In the following description, reference is made to the accompanying drawings which are provided for illustration purposes as representative of specific exemplary embodiments in which the invention may be practiced. The following illustrated embodiments are described in sufficient detail to enable those skilled in the art to practice the invention. It is to be understood that other embodiments may be utilized and that structural changes based on presently known structural and/or functional equivalents may be made without departing from the scope of the invention.

Given the following detailed description, it should become apparent to the person having ordinary skill in the art that the invention herein provides a novel liquid vaporization device and a method thereof for providing augmented efficiencies while mitigating problems of the prior art.

FIGS. 1A-1F illustrate various views of a vaporizer, or vaporizer device 100 in accordance with an embodiment of the present invention. In overview, the vaporizer device 100 includes an elongated tubular body 102 having at its upper end one or more liquid sample passage opening/ports 104 each associated with a passage or passageway 113 for introduction into an interior of the vaporizer device 100. The liquid sample ports 104 can include an axially disposed liquid sample introduction port 104A and one or more radially disposed liquid sample introduction ports 104R or just multiple radially disposed liquid sample introduction ports 104R. Unless specifically designated, the term liquid sample port 104 can apply to any one of the ports 104R and 104A. Further, in one embodiment, the vaporizer device 100 could include only a single radially disposed liquid sample introduction port 104R. When more than one opening/port 104 is included, discharge of liquified hydrocarbons, such as NGL or LNG, can be effected via one of the opening/ports 104. Once a liquid sample flows through an opening/port 104R through passageway 113 or through opening/port 104A, at least a part of the liquid sample flows to an axially and interiorly directed liquid sample channel 120 for communicating the liquid sample to a vaporizer core 130 formed of the space within an elongated, stepped bore 135 extending interiorly and axially from the lower end of the body 102 to the outlet of the channel 120. Upon vaporization of the liquid sample passing within the vaporizer core 130, the now-vaporized sample passes to vapor annulus 137 and through the radially oriented vapor outlet passageway 140 to exit the device via a vapor discharge outlet port 118. The vapor outlet port 118 is located proximate the lower end of the body 102.

Figure 1B:
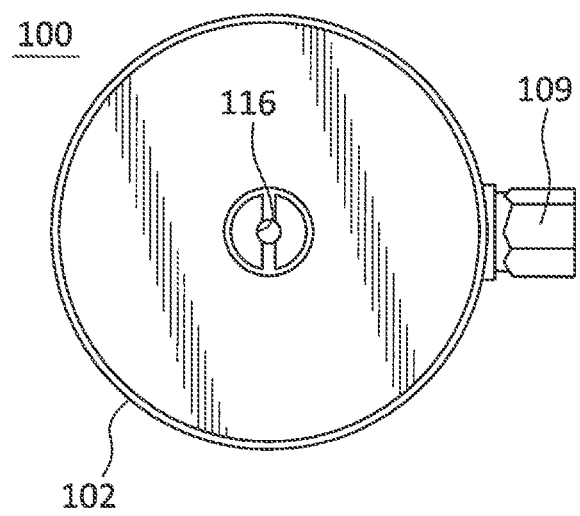
FIG. 1B is a top view of a vaporizer device in accordance with an embodiment of the present invention.
Figure 1C:
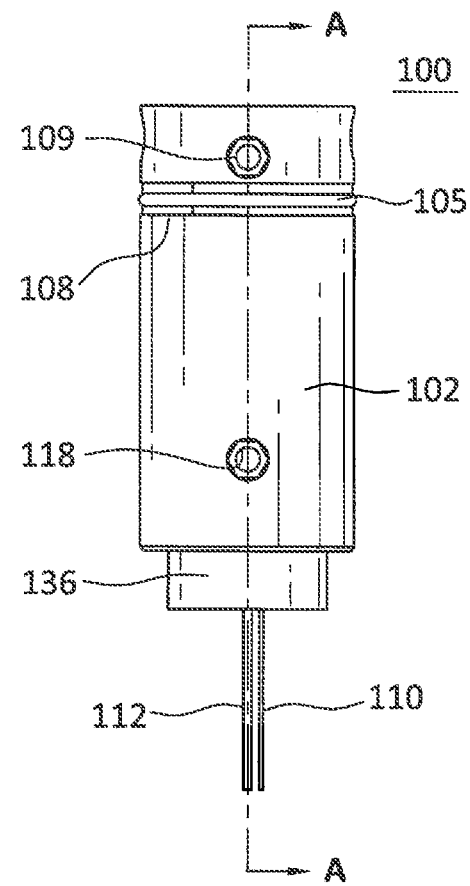
FIG. 1C is a side view of the vaporizer device in accordance with an embodiment of the invention.
Figure 1D:
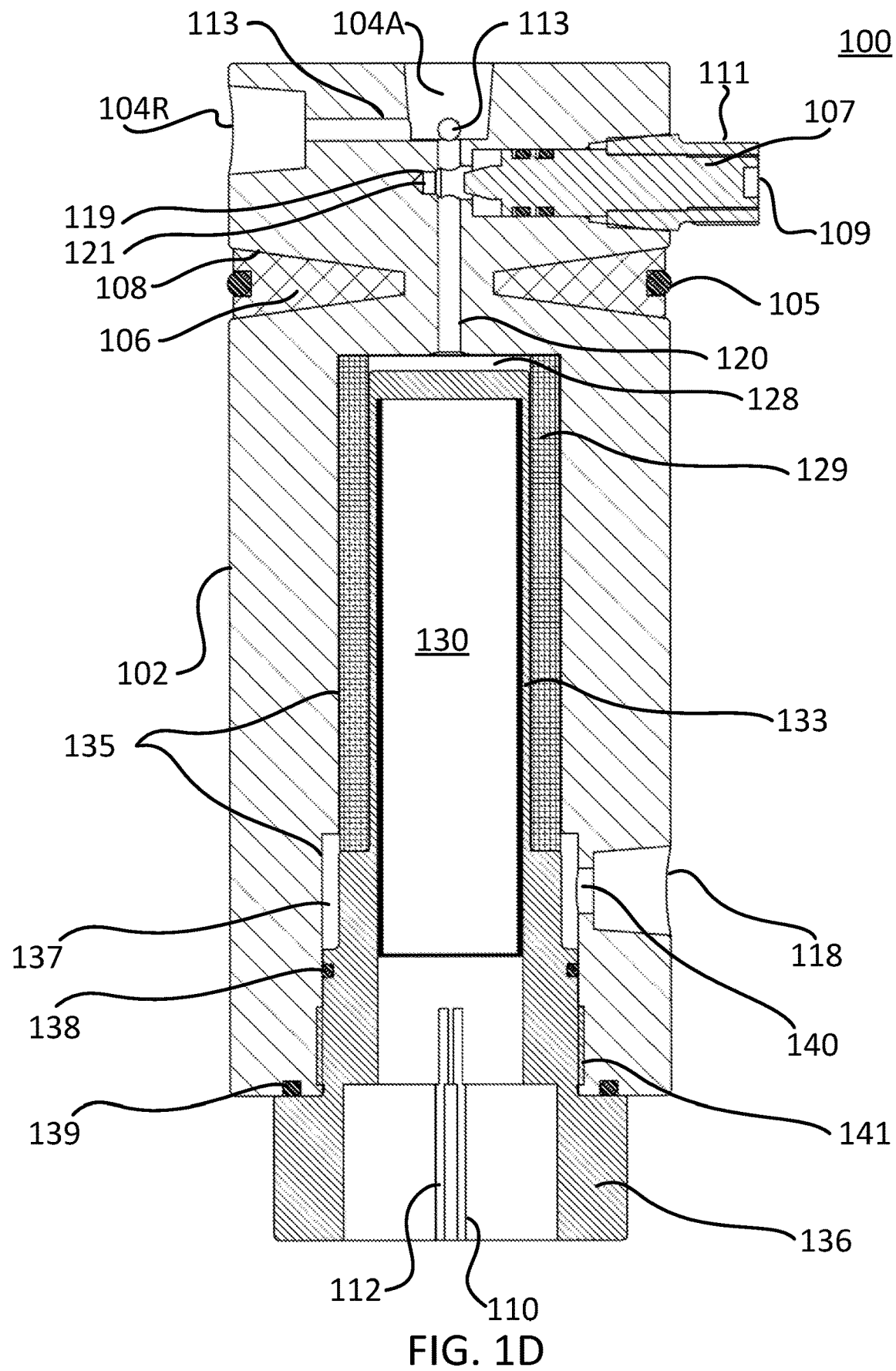
FIG. 1D is a two-dimensional view of the vaporizer device perspectively cut as illustrated in FIG. 1E in accordance with an embodiment of the invention.
Figure 1E:
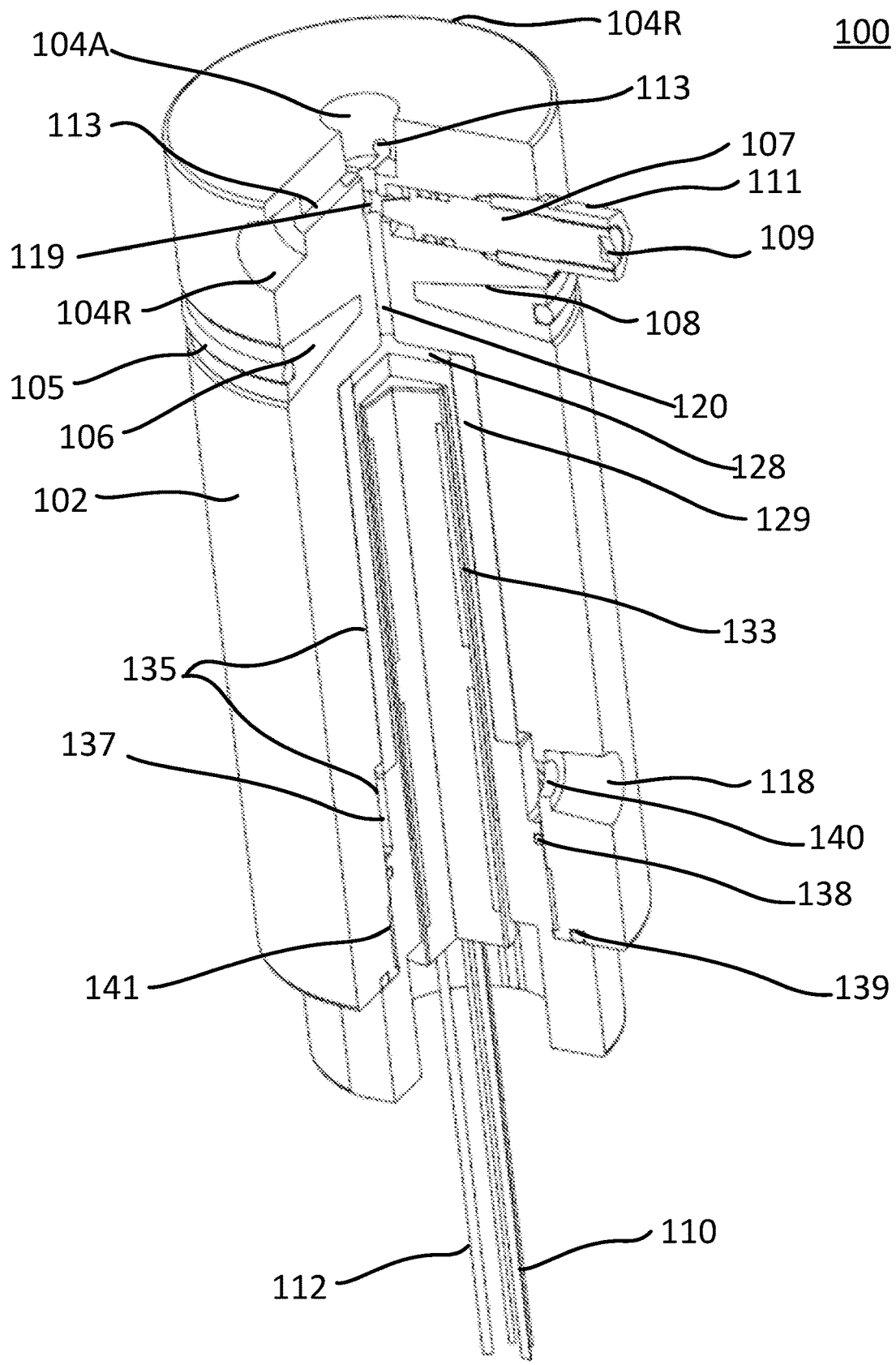
FIG. 1E is perspective cut-away view of the vaporizer device in accordance with an embodiment of the invention.

In FIGS. 1D and 1E, a dual port embodiment is illustrated in greater detail. As illustrated, liquid sample communication ports 104R and associated liquid sample passageways 113 may be disposed radially and diametrically aligned in a generally common, cross-sectional plane with respect to the body 102 or, may be disposed orthogonally when dictated by a particular geometry involving confined space limiting access. The ports 104R may be threaded for sealingly securing a fluid input line to the vaporizer device 100 with a mating fitting (not illustrated). Correspondingly, the vapor outlet port 118 may also feature internal threading for securing a gas output line via an appropriate fitting (not illustrated).

The geometry of a particular installation may lend itself to an axially disposed liquid sample introduction port 104A through the top of body 102. As illustrated in FIG. 1B, if unused, the axial port 104A disposed on a top portion of the body 102 can be sealed by a sealing screw/plug element 116. The port 104A may be threaded for sealingly securing a fluid input line to the vaporizer device 100 with a mating fitting (not illustrated). Regardless of the particular geometry, the embodiment contemplates introduction of a vaporizable liquid through a port 104 to an axially and interiorly directed channel 120 for liquid sample introduction to the vaporizer core 130 of the vaporizing device 100 for flash vaporization.

The liquid sample introduced to the vaporizer device 100 through a port 104 passes into the axial channel 120 for vaporization. It may be desirable to include a discharge port 104A/R to accommodate any liquid sample not passing to the vaporizer core 130. Accordingly, the embodiment provides for passage of unused liquid sample through a port 104A/R, acting as a discharge port, located with respect to the input port liquid 104A/R so as to minimize and/or avoid flow rate anomalies and the like generated by damming or backpressure. Accordingly, the presence of a second port 104 allows excess liquid entering the housing 102 through one inlet port 104 to exit as unvaporized liquid through another port 104 regardless of whether the inlet is radially or axially disposed.

Turning now to the interior of the vaporizer device 100, the liquid sample channel 120 extends axially for a select distance through the body 102 to establish a conduit for communicating the liquid sample from the passageway 113 to the vaporizer core 130. The depicted embodiments include a liquid flow control element, illustrated in the form of an adjustable valve 107 for controlling the volume of liquid sample flow. The adjustable metering valve 107 is mounted in a radially oriented bonnet 111 which is screwed into side of the body 102 and is disposed perpendicularly along the length of channel 120 and below the ports 104. The valve 107 features a tapering plunger 121 dimensioned for insertion into a seat 119 that intersects the channel 120. The degree of blockage by the metering valve 107 of the channel 120 flow path is adjustable via an adjustor element 109. The adjuster element 109 which may take the form of a slotted screw head, rotates relative to the mounting bonnet 111 to move the plunger of metering valve stem 107 radially relative to the channel 120. An automated alternative to the manual adjustor element 109 would involve the valve 107 being associated with an actuatable motor (not illustrated) to control adjustment of the position of the valve 107. The radially adjustable metering valve 107 has access to the channel 120 to adjust the volume of liquid flow sample which can make it easier for operators to control when accessing the vaporizing device 100 within, for example, sample conditioning panels. An alternative adjustable metering valve 402, of which could be incorporated into the vaporizer device 100 instead of the adjustable valve 107, bonnet 111, and tapering plunger 121, is discussed further with respect to FIGS. 4 and 5.

A notable feature of the instant embodiment relates to the exterior recessed, annular, thermal isolation gap 108 integrally formed in the body 102 and axially disposed between the liquid sample ports 104 and the vaporizer core 130 to form a first segment of the body 102 above the gap 108 and a second segment of the body 102 below the gap. To maximize its thermal isolating capability, the exterior annular gap 108 is defined generally as non-parallel surfaces extending a radial depth relative to the body 102 approaching the axial channel 120 toward the central axis of the device 100. In the illustrated embodiment of FIGS. 1A-1D, the upper and lower surfaces of the gap taper inwardly in a flat planar surface configuration. The respective upper and lower surfaces defining the gap may also possess alternative geometries such as arcuate, semi-circular, etc, which provide generally non-parallel surfaces that change the angle of heat radiation incidence and improve the reflective loss as compared with parallelly disposed facing surfaces. To provide enhanced thermal isolation of the upper end of the vaporizing device 100 from the vaporizer core 130, the illustrated embodiment is provided with a selectively removable passive thermal insulator 106. As illustrated, the passive thermal insulator 106 is bifurcated and retained in the gap by insulator retainer 105, such as a resilient o-ring. Alternatively, the thermal insulator 106 may be permanently situated in the gap 108 by molding or casting.

The non-parallel contouring or tapering of the thermal isolation gap 108 provides one or more of the following advantages including: 1) increasing the structural integrity and strength of the vaporizer body, particularly with respect to resisting increased pressures generated by liquid sample vaporization within the vaporizer core 130; 2) maximizing contact area between the surfaces of the thermal insulator 106 and the confronting surfaces of the tapering isolation gap 108 and minimizing potential separation by the applied compressive radial hoop force from the insulator retainer 105; 3) reducing the risk of condensation formation between the thermal insulator 106 and the body 102 at their interface in the isolation gap 108; 4) allowing the material forming the thermal insulator 106 to avoid tensile failure; and 5) improving radiant heat rejection through reflection by providing a larger aperture surface area. As described below with respect to FIG. 2, the thermal insulator 106 may optionally incorporate features to provide active cooling elements such as a subsystem based on a looped unheated liquid by-pass.

Moving to the physical characteristics of the passive thermal insulator 106, it is preferably composed from a dimensionally stable, relatively rigid, very low thermally conductive material such as foamed alumina or calcium silicate glass/fibers, foamed ceramic, etc. The material is formed/molded into a trapezoidal, toroidal configuration dimensionally corresponding to the conformation of the gap 108. The insulator 106 can be cut into two confrontable mating pieces each featuring a central cutout/kerf dimensionally corresponding to the axial segment through which the channel 120 passes in the body 102. Consequently, the thermal insulator 106 establishes thermal isolation between the upper and lower portions of the body 102 by way of the tapered thermal isolation gap 108 and minimizes the risk of undesirable liquid sample pre-vaporization before it reaches the vaporizer core 130. By minimizing and/or eliminating heat migration from the vaporizer core 130 to the upper portion of the body 102, pre-vaporization above the vaporizer core is reduced which leads to enhanced sample uniformity and increased accuracy of sample analysis. Furthermore, the issue of ice formation on the exterior of the body 102 proximate to the ports 104 attributable to such pre-vaporization is reduced.

Figure 1F:
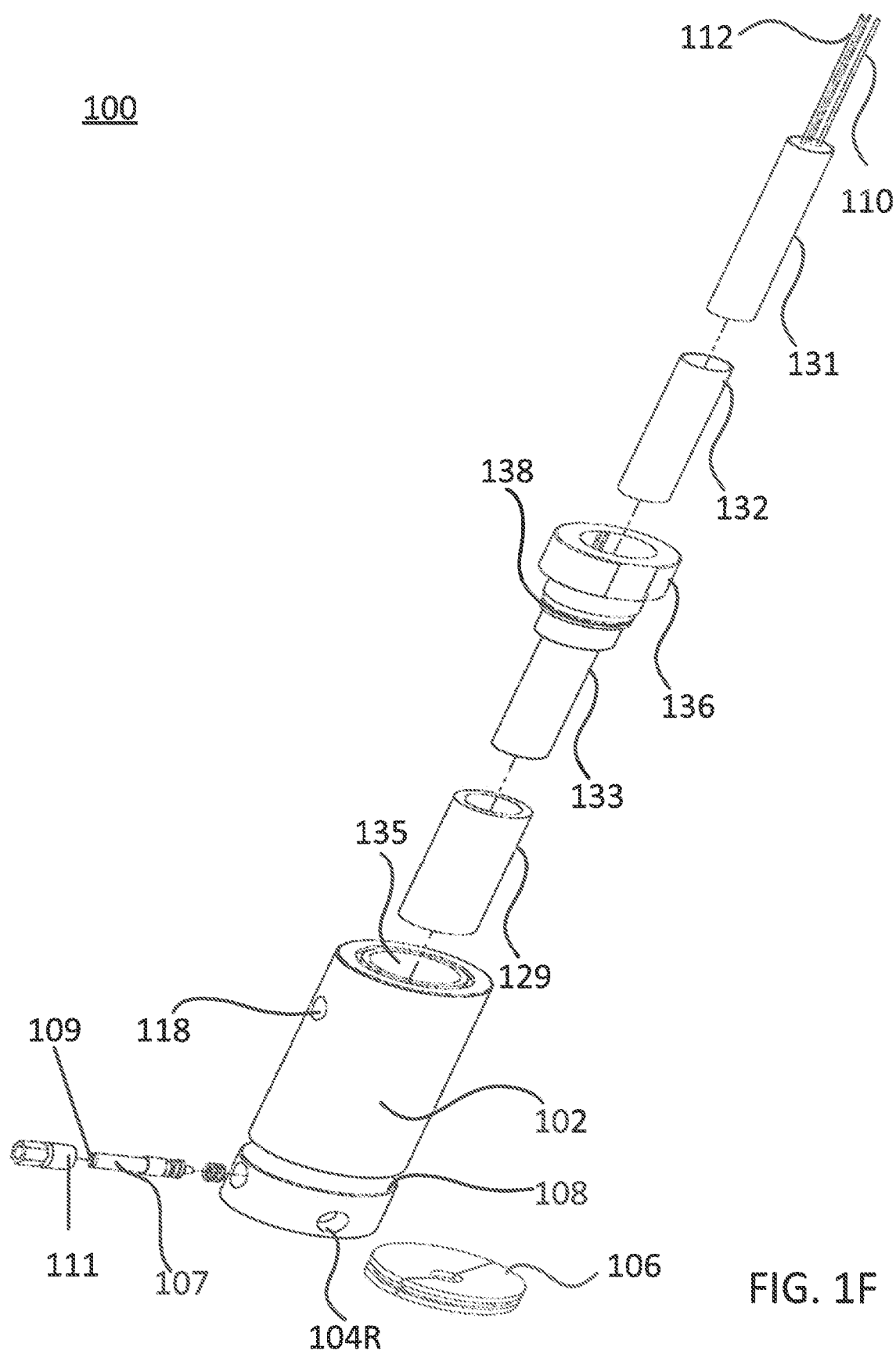
FIG. 1F is perspective exploded view of the vaporizer device in accordance with an embodiment of the invention.

Turning now to the vaporization elements associated with the vaporizer core 130 when the vaporizer device 100 is fully assembled, and referring particularly to FIG. 1F, the vaporizer core 130 encloses a heating assembly that can include an insertion cartridge heater or heating element 131, an optional metal sheath 132 made of brass, copper or another material for conducting heat and an overlying heater housing 133 made of stainless-steel or other metal. The insertion cartridge heater 131 is powered by electrical feed lines 112 and controlled via a thermocouple 110 both projecting from the base of the body 102. Alternatively, or in addition to, the body 102 may feature a bore and/or protrusion near the outlet port 118 to accommodate a thermowell having an additional thermocouple that detects the temperature of the vaporized sample leaving the vaporizer as described further with respect to FIGS. 4 and 5.

The thermocouple 110 is connected to a proportional-integral-derivative (PID) controller and/or Programmable Logic Controller (PLC) (not shown), such as an Allen Bradley 850 series PLC or equivalent controller, to provide signal feedback and control of the vaporizer device 100. The metal sheath 132 engirds the cartridge heater 131 to promote uniform distribution of heat from the heater 131 to the overlying stainless-steel heater housing 133. The sheathed cartridge 131 is seated snuggly, preferably by compression and, in turn, the stainless-steel housing 133 dimensionally conforms to the inner surfaces of the stepped bore 135 for insertion therein. The upper end of the stainless-steel heater housing 133 has a diameter less than that the vaporizer core 130 and projects to an axial position leaving a gap 128 to permit liquid sample flow from the channel 120 to an area between an outer surface of the heater housing 133 and an inner surface of the bore 135. The diameter of the non-reactive housing 133 is stepped diametrically from the upper end to the lower end in a fashion to accommodate a foraminous non-reactive, stainless steel wire mesh 129, a stepped ring to establish the vapor annulus 137 between the body 102 and the stainless steel housing 133, and a mounting fixture 136 for secure, sealing attachment to the body 102.

The foraminous non-reactive, stainless steel wire mesh 129 is disposed about the upper step portion of the heater housing 133 and dimensioned to fill the area between the step of the housing 133 and the interior surface of the bore 135. Flash vaporization is achieved upon liquid sample contact with the wire mesh by efficient transfer of heat energy from the electrical cartridge heater 131 via the heat distribution sheath 132 to and uniformly through the non-reactive housing 133. The wire mesh 129 provides a variety of advantages. First, utilization of the wire mesh 129 tends to maximize and otherwise provide a very large heat transfer surface area for transferring heat outwardly from the housing 133 to obtain uniform liquid flow and vaporization, and an essentially homogeneous vapor that is representative of the liquid sample composition.

More specifically, the mesh 129 acts as a diffuser which aids in the formation of uniform flow passing through the housing 102 and at the outlet 118. This uniform flow enhances the heating and ultimate vaporization of liquids while also reducing hot spots and the formations of deposits within the vaporizer core 130. Further, the mesh 129 acts as a thermal transfer path thereby allowing heat to be carried away from the heater housing 133 and into the fluid flow path between the housing 133 and the inner surface of the bore 135. The mesh 129 also encourages mixing which promotes thermal transfer to fluid passing through and around the mesh 129. Accordingly, the use of the mesh 129 having augmented heat characteristics from the housing 133 effectively increases the surface area of heated liquid in the cavity between the housing 133 and the inner surface of the bore 135. Further, the transfer of fluid through and around the mesh 129 impedes the egress of liquid from the vaporizer core 130 thereby ensuring adequate heating of the traveling liquid. These advantageous features provide for enhanced vaporization of liquids passing through the vaporizer core 130 thereby reducing or eliminating the output of unvaporized liquid which could damage a downstream analyzer.

Use of the mesh 129 or highly porous material maximizes the surface area for heat transfer to the cascading input liquid sample, which in the case of LNG results in a 600-fold volumetric expansion, and also establishes a vapor transit passage to exit though the vapor annulus 137 into the vapor outlet passage 140 and to the vapor sample discharge port 118. Where pre-formed as a tubular element, the mesh 129 should be dimensioned to possess thickness sufficient to fill all space between an outer surface of the upper end of the housing 133 and the inner surface of the bore 135 below the gap 128 such that the mesh 129 maintains contact with both the housing 133 and the interior surface of the bore 135. In one embodiment, the mesh 129 may be crimped and spirally wrapped about the housing 133 to permit some radial compression upon insertion into the stepped bore 135. Once inserted into the stepped bore 135, the mesh 129 can be allowed to unwrap thereby filling the area between the outer surface of the housing 133 and the interior surface of the bore 135.

Figure 1G:
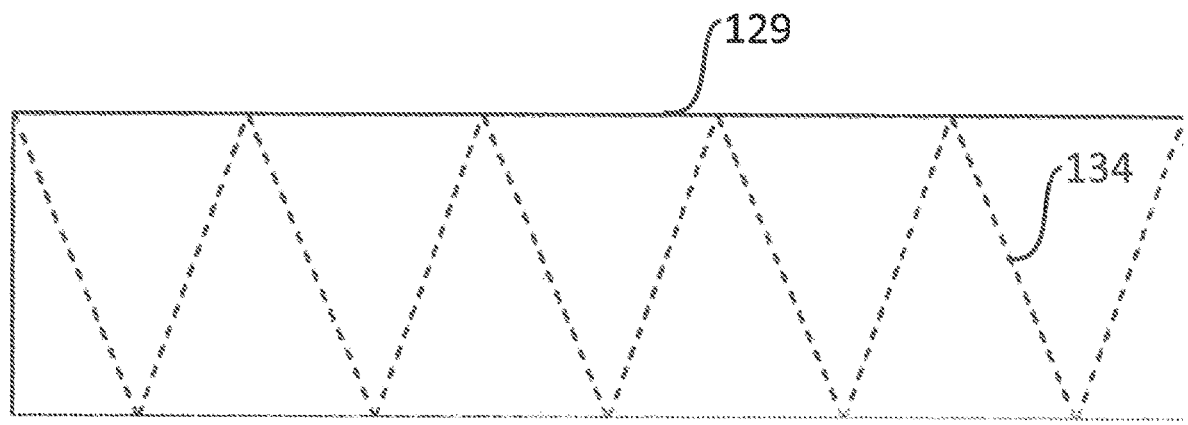
FIG. 1G is a side view of wire mesh in accordance with an embodiment of the invention.

In one embodiment, the mesh 129 can be uniformly bent as illustrated in FIG. 1G. In this example, the mesh 129 is provided with a series of alternating bends 134 formed so that when the mesh is coiled around the housing 133, the bends 134 do not nest within each other on subsequent wraps. Nesting of the bends 134 is undesirable as it both prevents the mesh 129 from expanding and also reduces the ease of installation and adjustment of the mesh 129. By providing a non-parallel linear bend to either edge of the mesh 129 (when uncoiled), and repeating the bend in an alternating direction across the mesh length, the mesh 129 concomitantly avoids nesting and expands substantially uniformly to fill the area between the outer surface of the housing 133 and the inner surface of the bore 135.

The housing 102 also includes a first axially disposed o-ring seal 138 located proximate to and between the collecting annulus 137 and interior threading 141 formed at the base of the stepped bore 135 for threadedly co-acting with mating threading on the exterior surface of the stainless-steel housing 133 to seal the vaporizer core 130 within the body 102. To further ensure a complete seal to prevent any leakage of vaporized gas, the annular face of the body 102 may include an o-ring 139 for compression against confronting mating face of the stainless-steel heater body of the mounting fixture 136. In the illustrated single path version of the vaporizer device 100, the liquid sample is introduced to the vaporizer device 100 via a port 104 (a portion of which enters the channel 120 at a rate dictated by the metering valve stem 107), passes through the thermal separation zone defined by the gap 108, to the vaporizer core 130 to flash vaporize and pass, under the pressure of vaporization, into the collecting annulus 137 to exit the vaporizer through port 118.

Accordingly, pre-vaporization of a liquid sample introduced at the upper portion of the vaporizer device is avoided by thermally isolating the upper portion from the flash vaporization core 130 of the vaporizer device 100.

The vaporizer housing 102 can be crafted from a single unit of a corrosion-resistant super alloy such as stainless-steel or aluminum. The vaporizer core 130 can be step-bored from a bottom portion of the housing 102 using a boring bar on a lathe to radially provide space within the housing 102 for the annulus 137 and wire mesh 129. The axial length of the vaporizer core 130 is bored to a length which is slightly more than the axial length of the housing 133 such that when the housing 133 is fitted within the vaporizer core 130, a gap 128 is formed between the top of the housing 133 and the output of the channel 120. The channel 120 can be bored using a drill bit passing through the already-bored vaporizer core 130 and extends to the axial port 104A which is axially bored from the top of the housing 102. Radial ports 104R can be radially bored from the side of the housing 102 and passageways 113 can be bored with smaller bits using the already bored radial ports 104R to connect the radial ports 104R to the axial port 104A and the channel 120. Another bore is formed between the ports 104 and the isolation gap 108 along the axial length of the housing 102 in order to provide for the adjustable valve 107. This bore can then be used to machine a stepped bore orthogonally formed across a cross-section of the channel 120 thereby providing a seat for the valve 107 to control flow within the channel 120.

Figure 2A:
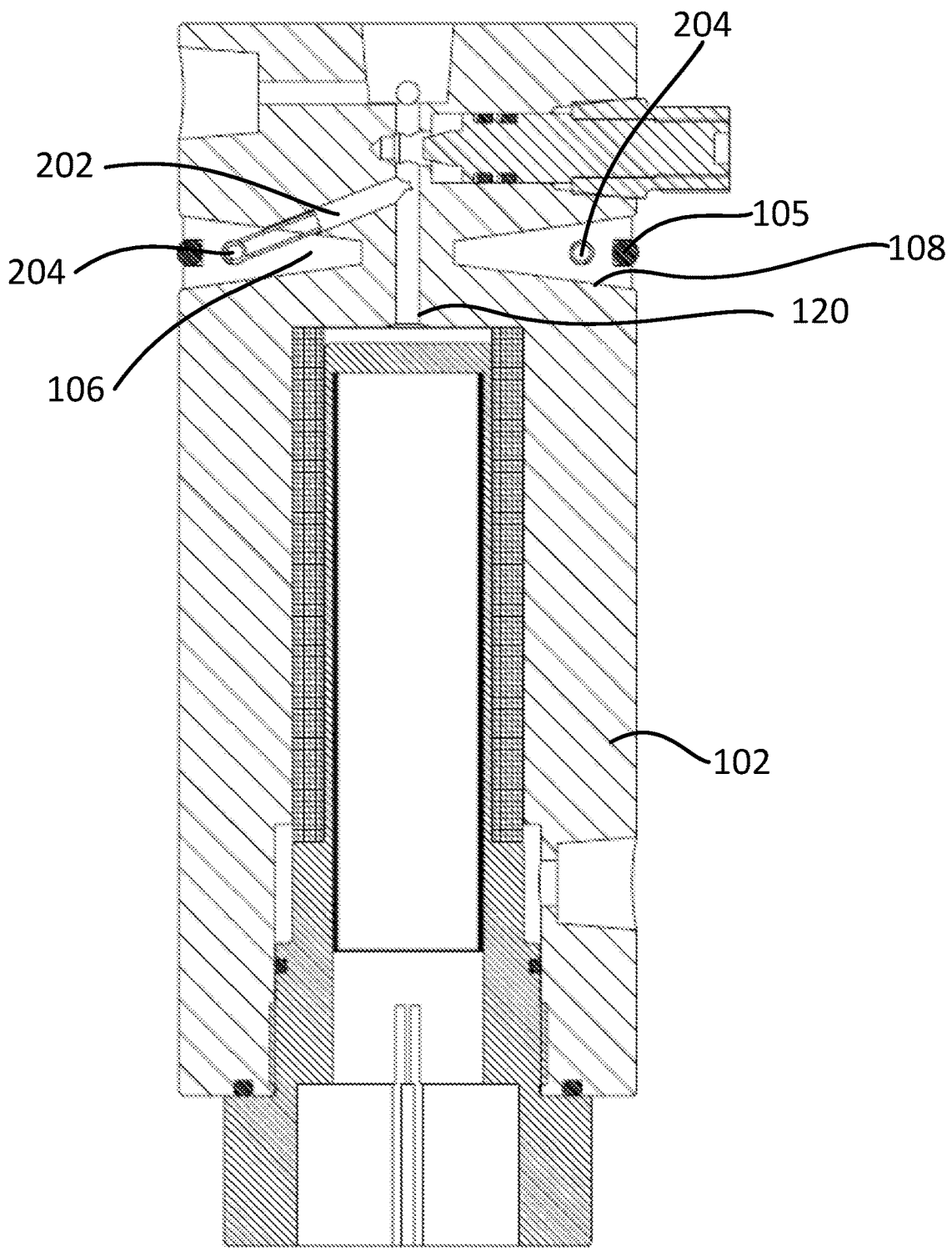
FIG. 2A is a cross-sectional view of a vaporizer device with an active cooling element along the bisecting line of FIG. 1C in accordance with an embodiment of the invention.
Figure 2B:
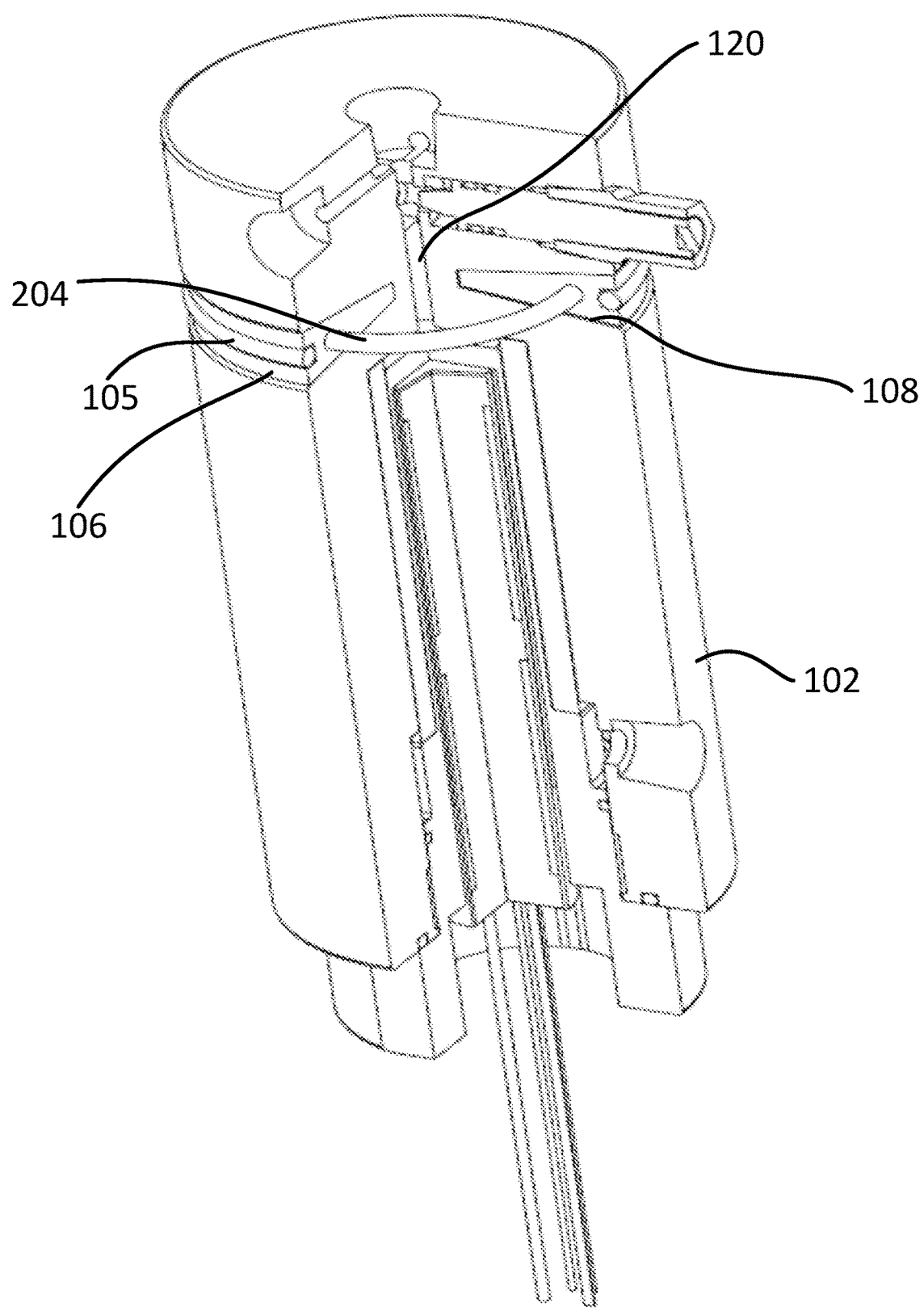
FIG. 2B is perspective cut-away view of the vaporizer device in FIG. 2A in accordance with an embodiment of the invention.
Figure 3A:
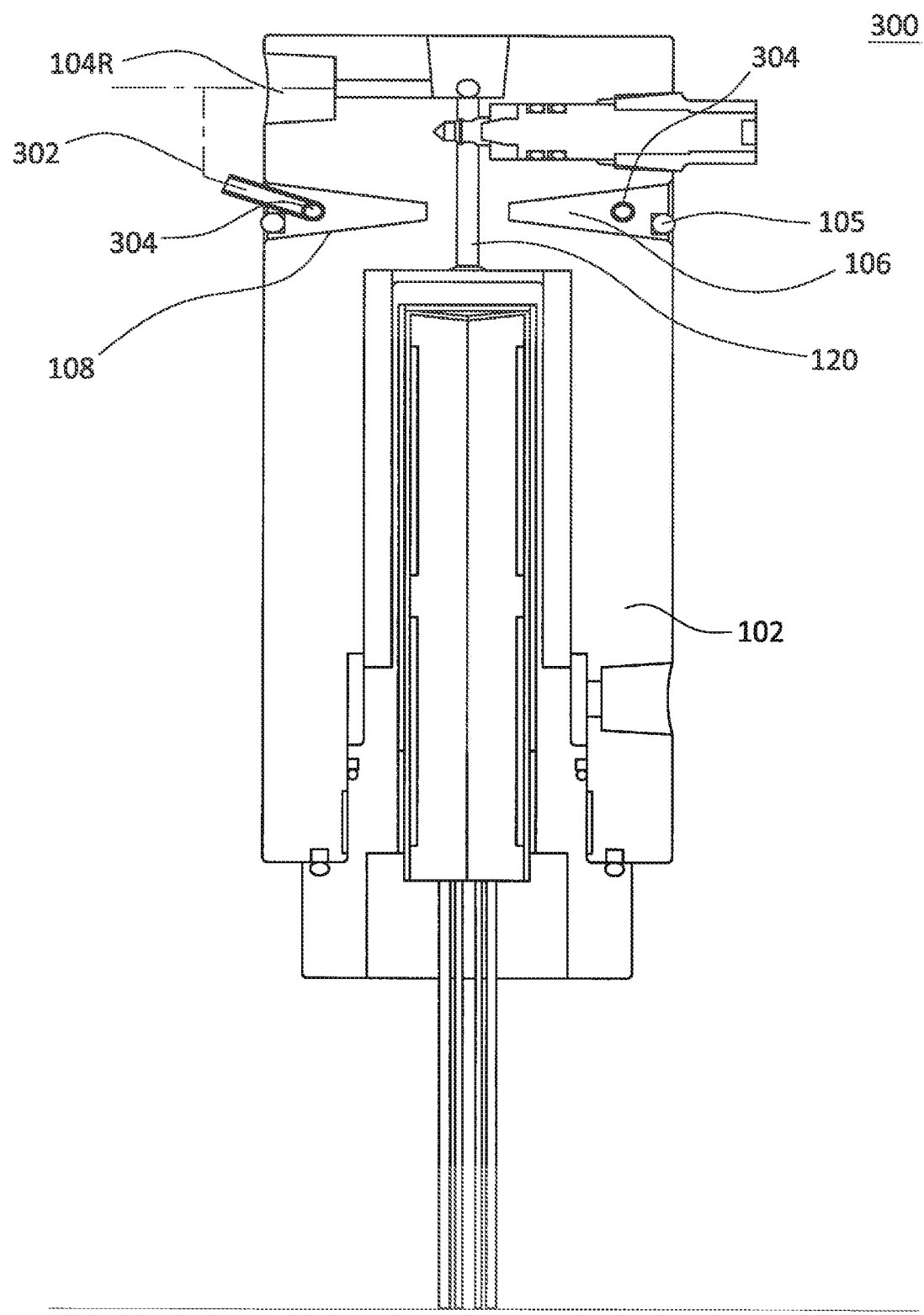
FIG. 3A is a cross-sectional view of a vaporizer device having an alternative active cooling element in accordance with an embodiment of the invention.

In FIGS. 2A/2B and FIGS. 3A/3B, active cooling embodiments of vaporizer devices 200 and 300 are respectively illustrated. The embodiments illustrated in FIGS. 2A/2B and 3A/3B are similar to the embodiment illustrated in FIG. 1 but further feature an active cooling adjunct to insure against heat transfer to the upper portion of the vaporizer and pre-vaporization of the liquid sample. FIGS. 2A and 2B illustrate an integrated flow channel take-off 202 from channel 120 located above the isolation gap 108 to provide for liquid flow to a loop 204 formed in thermal insulator 106. Accordingly, in this embodiment, a portion of the liquid introduced into channel 120 flows through the channel 202 to the loop 204 to provide an active cooling component to the insulator 106. An outlet (not illustrated) for the liquid passing through loop 204 may be connected to a liquid discharge port 104 or recirculated into the liquid feed stream at an input port 104R or passageway 113.

Figure 3B:
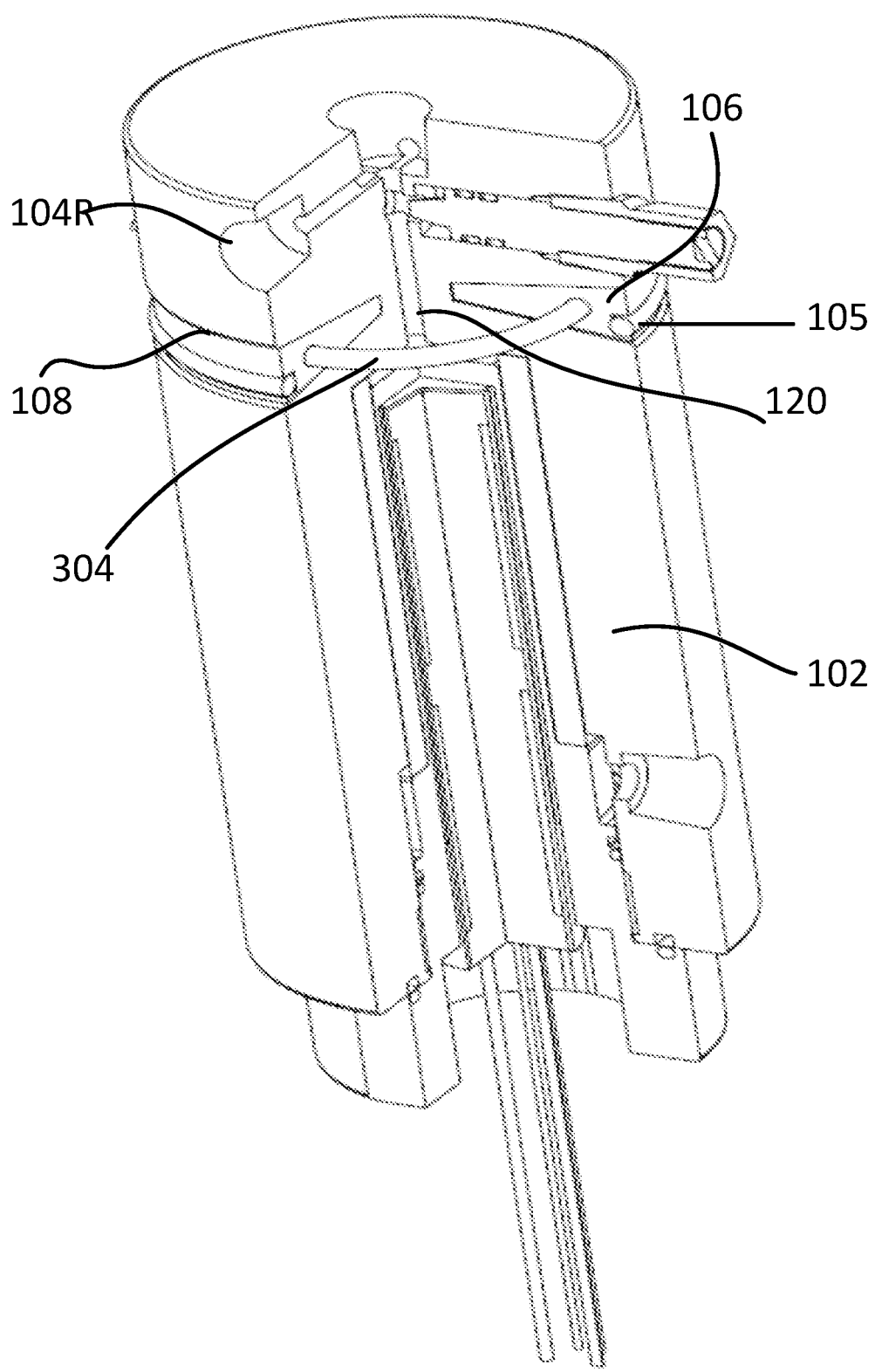
FIG. 3B is perspective cut-away view of the vaporizer device in FIG. 3A in accordance with an embodiment of the invention.

In FIGS. 3A and 3B, an active cooling loop take-off 302 (represented by dotted lines) is connected at an input port 104R to provide liquid sample to a tube 304 embedded in and encircling the insulator 106. The outlet of the tube 304 (not illustrated) can be connected to another liquid discharge port 104R from the vaporizer device 300 to provide a continuous flow of cooling liquid therethrough. In this case, the takeoff is provided by a flow channel takeoff proximate to the input port 104R wrapping around and embedded in an annulus formed in the insulator 108. Unheated liquid is taken off at the input at the inlet port 104R passed through the active cooling circuit, illustrated as a tubular loop with a liquid fluid tube, to a drain/outlet (not illustrated) connected to a discharge speed loop or the like. In this manner a fresh supply of cooling liquid can be utilized to augment cooling to prevent the upper portion of the body 102 from heating. Thus, the risk of pre-vaporization before entry of the liquid sample to the vaporizer core 130 is minimized.

Figure 4A:
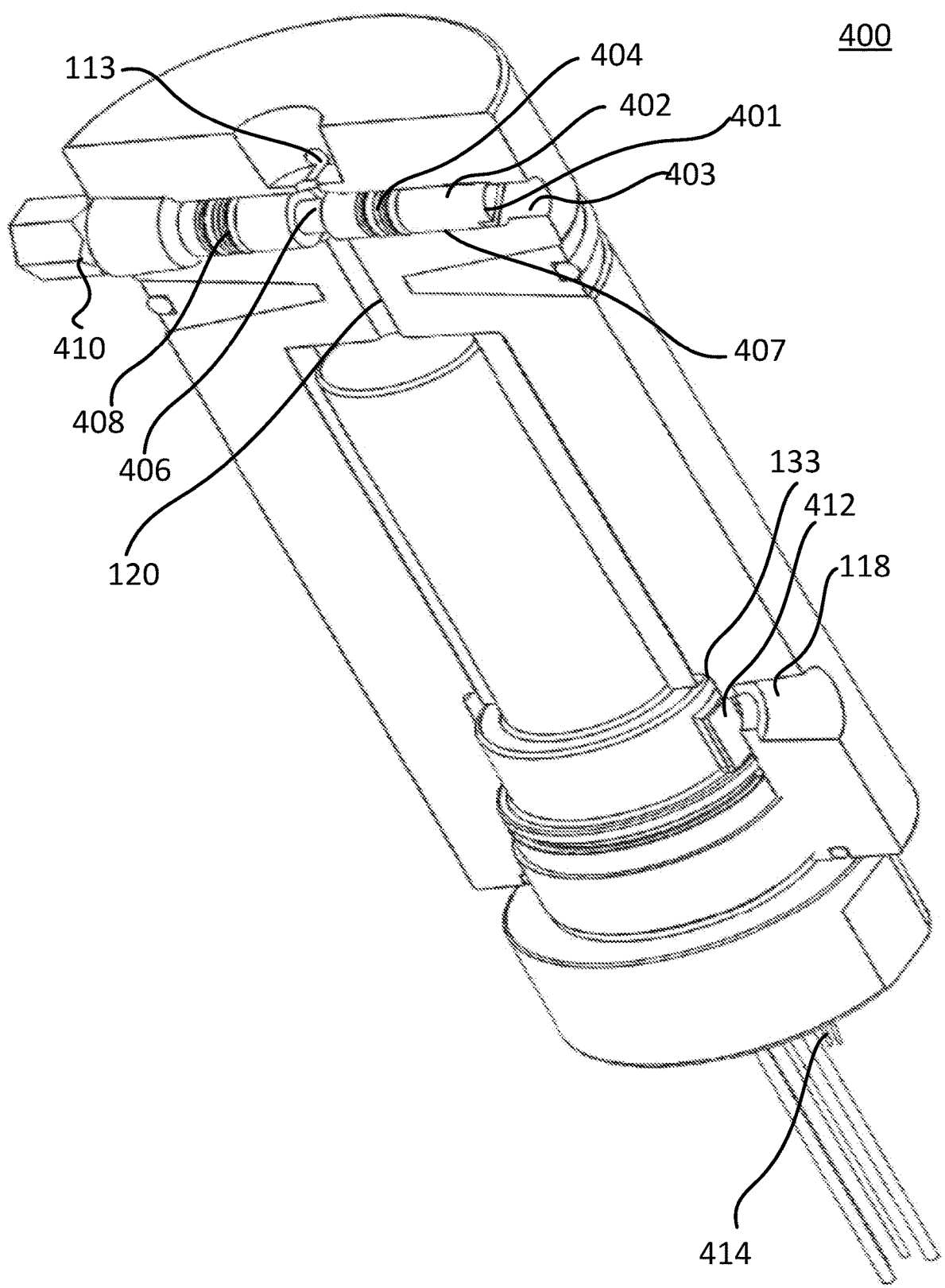
FIG. 4A is a perspective cut-away view of a vaporizer device having an alternative metering valve in accordance with an embodiment of the invention.

FIG. 4A is a perspective cut-away view of a vaporizer device 400 having an alternative tapered metering valve stem 402 in accordance with an embodiment of the invention. The tapered metering valve stem 402 is provided within a cavity 403 radially bored into the body 102 axially between the passageway 113 and the thermal isolation gap 108. The tapered metering valve stem 402 can include thereon a plurality of o-rings 404, 408, or the like, that seal and provide pressure control within the cavity 403. The cavity 403 can include a threaded portion 407 allowing for the tapered metering valve 402 to rotate and radially traverse a predetermined distance within the cavity 403. The tapered metering valve stem 402 further includes a substantially central groove 406 which is circumferentially tapered to a reduced diameter with respect to surrounding portions of the tapered metering valve 402 stem thereby allowing liquid to flow around the metering valve stem 402 and through throat or channel 120. The degree of blockage by the tapered metering valve stem 402 of the channel 120 flow path is adjustable via an adjustor element 401. The adjuster element 401 which may take the form of a slotted screw head, rotates relative to the threading 407 to translate the groove 406 of the metering valve stem 402 radially relative to the channel 120. Thus, the amount at which liquid flow is controlled is dictated by a location of the tapered groove 406 with respect to the channel 120. An automated alternative to the manual adjustor element 401 would involve the metering valve stem 402 being associated with an actuatable motor (not illustrated) to control adjustment of the position of the valve stem 402. A cap or plug 410 is provided at an end of the metering valve 402 opposite the adjustable element 401 to enclose the cavity 403, prevent pressure-induced expulsion of the metering valve stem 402 and limit the travel of the metering valve 402 within the cavity 403. The cap or plug 410 can be external to the vaporizer device or included within the cavity 403 such that it is flush with the body 102.

Figure 4B:
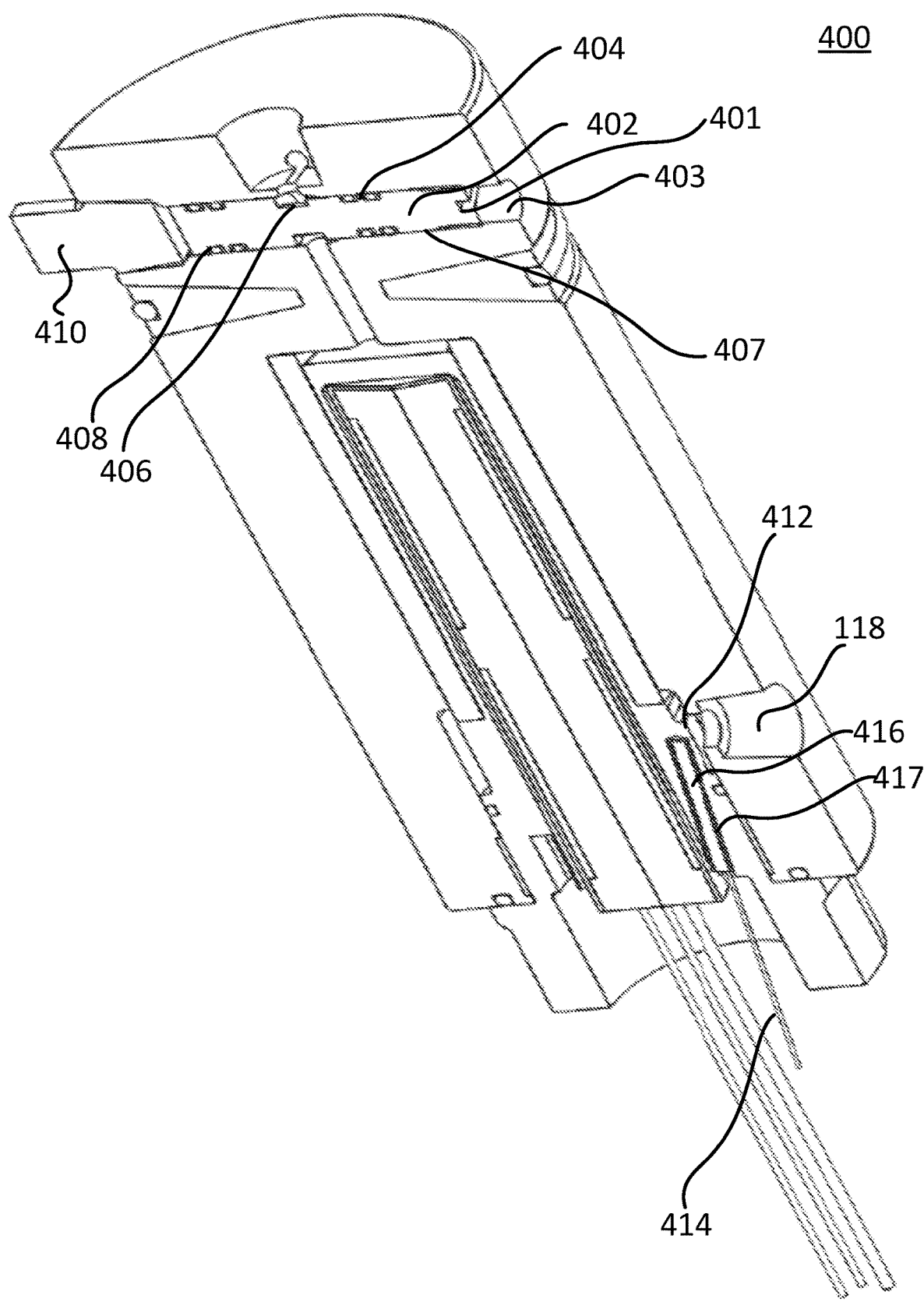
FIG. 4B is a perspective cut-away view of the vaporizer device of FIG. 4A having an angled thermowell and associated thermocouple in accordance with an embodiment of the invention.

FIG. 4B is a perspective cut-away view of the vaporizer device 400 having the tapered metering valve 402 in accordance with an embodiment of the invention. Here, the tapered metering valve 402 is the same as that described with respect to FIG. 4A and therefore like designations are repeated. However, it should be noted that the implementation of the adjustable metering valve 107 of the vaporizer device 100 illustrated in FIGS. 1D-1F could be incorporated into the vaporizer device 400 instead of the tapered metering valve 402 structure.

Also illustrated in FIG. 4B is the inclusion of an additional thermocouple 416 proximate the outlet port 118 and provided within a thermowell 417 formed within a protrusion, such as a machined boss 412, protruding from the heater housing 133 as illustrated in FIG. 4A. The thermowell 417 is angled such that an upper portion of the thermowell 417, and thermocouple 416 therein, are positioned proximate the outlet port 118 at a high velocity flow region to provide enhanced sensitivity and more accurate readings as to the temperature of gas samples exiting the vaporizer device 400. The presence of the machined boss 412 increases the temperature sensitivity without restricting the flow rate in any substantial manner.

As with the thermocouple 110, the thermocouple 416 can be connected via lead 414 to a proportional-integral-derivative (PID) controller and/or Programmable Logic Controller (PLC) (not shown), such as an Allen Bradley 850 series PLC or equivalent controller, to provide signal feedback and control of the vaporizer device 400. This allows for the creation of a control loop for continuously monitoring and controlling the temperature of gas samples exiting the vaporizer device 400. Accordingly, based on the equipment that is connected to the vaporizer device 400, the temperature can be controlled to ensure that gas exiting the vaporizer device 400 will not damage the downstream equipment. The inclusion of the thermocouple 416 proximate the outlet port 118 also provides the advantage of being able to monitor undesirably high temperatures that could be the result of a no flow condition in which no liquid is flowing through the vaporizer device 400. Thus, the interiorly positioned thermocouple 416 improves upon remote sensing of the outlet gas temperature with a sensing device attached to the outlet as such a remote device would not be able to detect high heater temperatures resulting from a no flow condition thereby risking a burnout that could destroy the heating element and render the vaporizer device 400 inoperative. The installation of the thermocouple 416 within the housing also provides for less failure modes during assembly of the vaporizer device 400 while also providing for simpler wiring to the control system which often times requires meeting explosion proof design code.

Figure 5A:
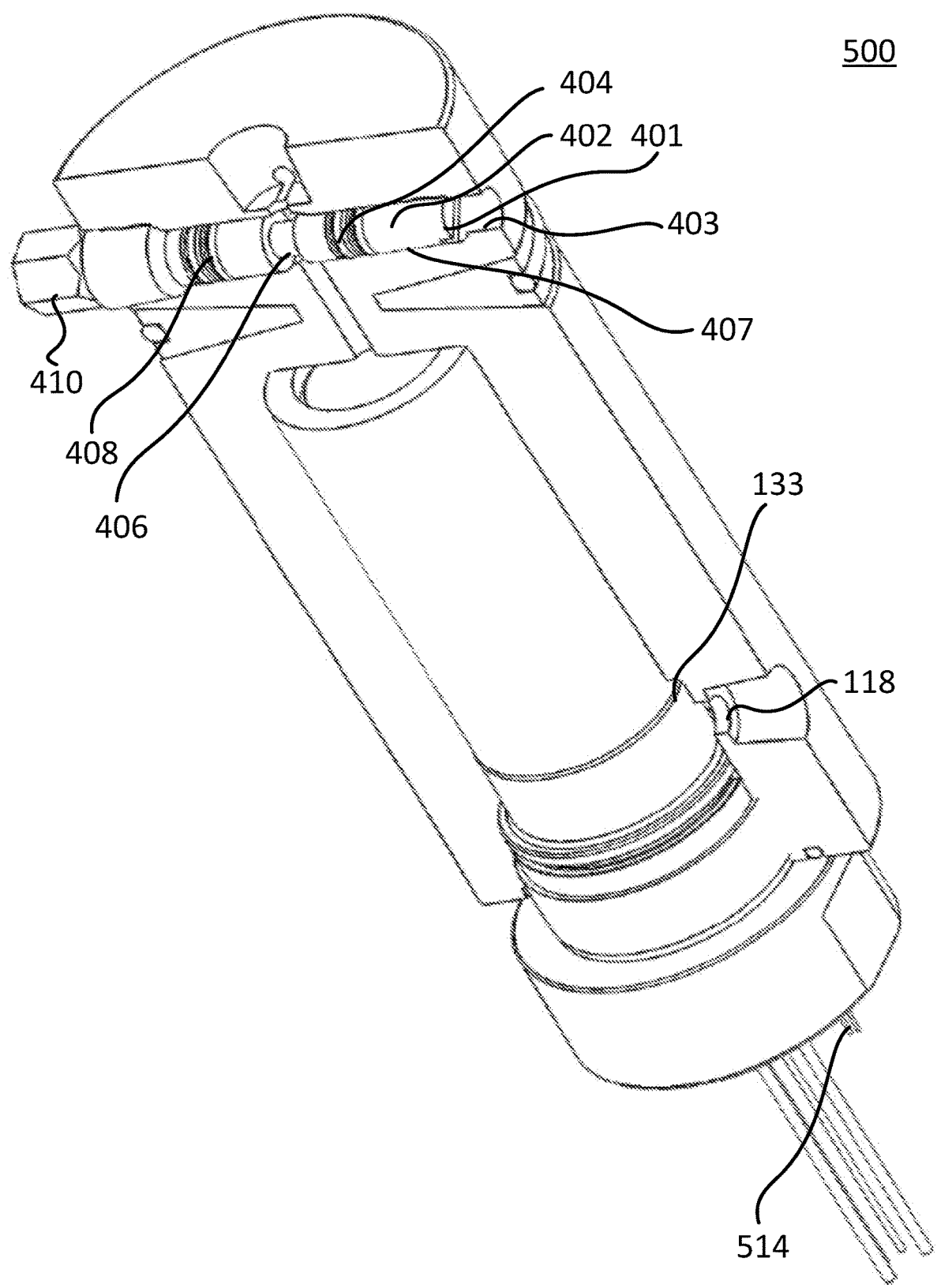
FIG. 5A is a perspective cut-away view of a vaporizer device having a straight thermowell and associated thermocouple in accordance with an embodiment of the invention.
Figure 5B:
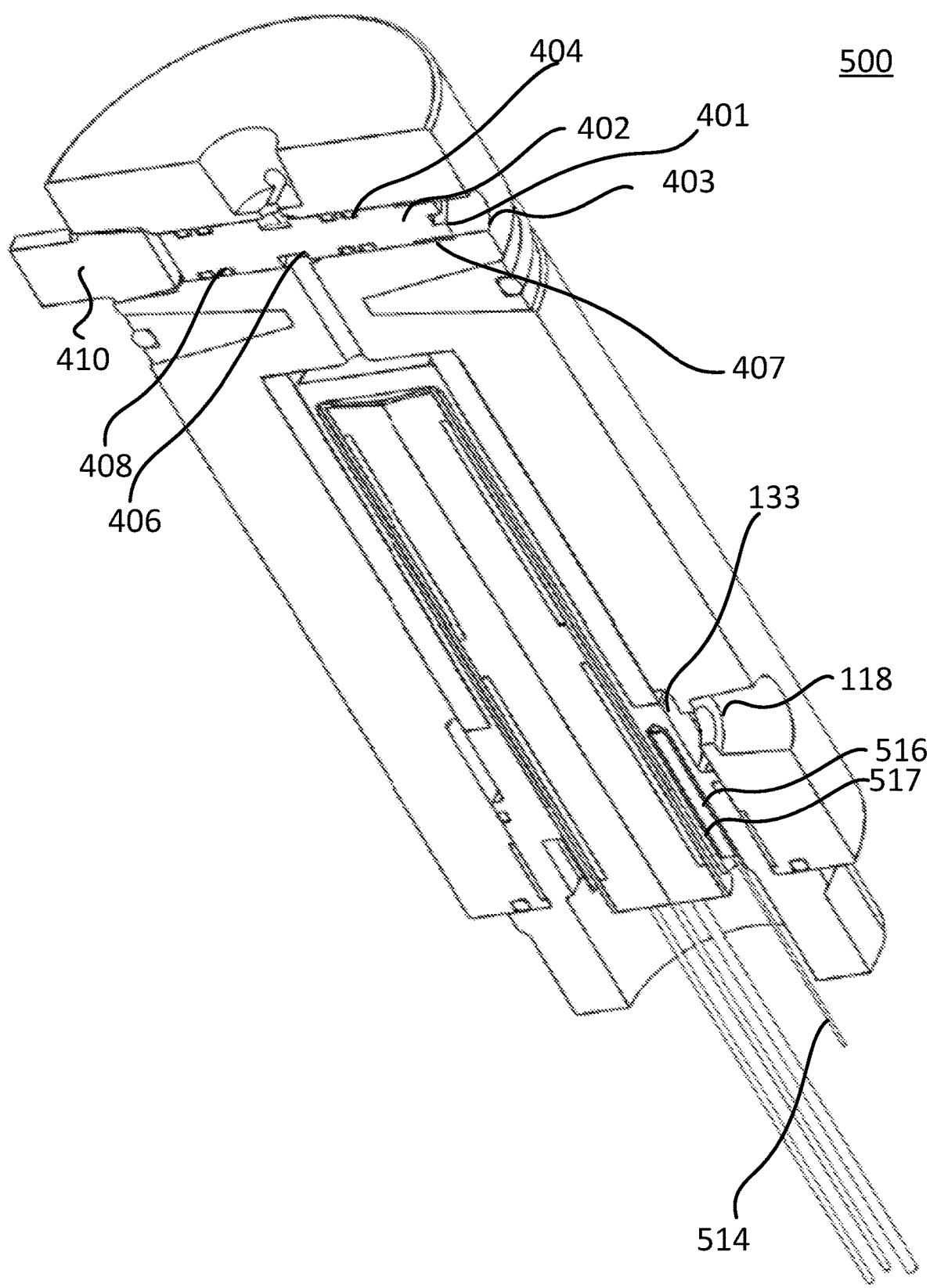
FIG. 5B is a perspective cut-away view of the vaporizer device having the straight thermowell and associated thermocouple in accordance with an embodiment of the invention

FIGS. 5A and 5B are perspective cut-away views of a vaporizer device 500 having the metering valve 402 in accordance with an embodiment of the invention. Here, the tapered metering valve 402 is the same as that described with respect to FIG. 4A and therefore like designations are repeated. However, it should be noted that the adjustable metering valve 107 of the vaporizer device 100 illustrated in FIGS. 1D-1F could be incorporated into the vaporizer device 500 instead of the tapered metering valve 402 structure.

Also illustrated in FIGS. 5A and 5B is the inclusion of an additional thermocouple 516 proximate the outlet port 118 and provided within a straight thermowell 517 formed within the heater housing 133. The thermowell 517 is axially bored so as to run parallel with the housing 133 and proximate the outlet port 118. A thermocouple 516 provided within the thermowell 517 is positioned proximate the outlet port 418 at a high velocity flow region to provide enhanced sensitivity and readings as to the temperature of gas samples exiting the vaporizer device 500.

As with the thermocouple 110, the thermocouple 516 can be connected via lead 514 to a proportional-integral-derivative (PID) controller and/or Programmable Logic Controller (PLC) (not shown), such as an Allen Bradley 850 series PLC or equivalent controller, to provide signal feedback and control of the vaporizer device 500. This allows for the creation of a control loop for continuously monitoring and controlling the temperature of gas samples exiting the vaporizer device 500. Accordingly, based on the equipment that is connected to the vaporizer device 500, the temperature can be controlled to ensure that gas exiting the vaporizer device 500 will not damage the downstream equipment. The inclusion of the thermocouple 516 proximate the outlet port 118 also provides the advantage of being able to monitor undesirably high temperatures that could be the result of a no flow condition in which no liquid is flowing through the vaporizer device 500. Thus, the interiorly positioned thermocouple 516 improves upon remote sensing of the outlet gas temperature with a sensing device attached to the outlet as such a remote device would not be able to detect high heater temperatures resulting from a no flow condition thereby risking a burnout that could destroy the heating element and render the vaporizer device 500 inoperative. The installation of the thermocouple 516 within the housing also provides for less failure modes during assembly of the vaporizer device 500 while also providing for simpler wiring to the control system which often times requires meeting explosion proof design code.

It should be appreciated that other well-known cooling adjuncts may be utilized in lieu of the above-described active cooling subsystem. The perceived advantage of the above-described systems is that they rely on the simple expedient of diverting a small amount of the liquid takeoff sample for cooling and either reinjecting that diverted amount back into the pipeline or passing it though any one of well-known collection/recirculation systems.

It should be understood for a person having ordinary skill in the art that a device or method incorporating any of the additional or alternative details mentioned above would fall within the scope of the present invention as determined based upon the claims below and any equivalents thereof. Other aspects, objects and advantages of the present invention should be apparent to a person having ordinary skill in the art given the drawings and the disclosure.

What is claimed is:

1. A vaporizer for vaporizing a multi component hydrocarbon containing liquid mixture, comprising:
   a generally elongated tubular body having a first segment defining a first end and a second segment defining a second end;
   a liquid sample port connected to a liquid passage formed integrally in the first segment, where said liquid sample port provides for liquid input;
   a liquid channel disposed generally longitudinally along a central axis of the vaporizer and extending substantially in the direction of elongation of said tubular body, said liquid channel having a first end and a second end, said first end of said liquid channel intersecting with said liquid passage to provide a flow path for liquid from said liquid sample port therethrough along its length;
   a liquid flow control element integrated within said first segment of said tubular body and configured to intersect the liquid channel;
   a gap formed in and extending from an exterior surface of the tubular body, the gap defining a generally non-parallel surface directed inwardly toward the liquid channel and disposed along the length of the liquid channel;

a vaporizer core with a stepped bore internal to and extending from said second end of said tubular body to said second end of said liquid channel;

a heating assembly dimensioned for insertion into the vaporizer core and sealingly securable to said tubular body, said heating assembly having a flash vaporizing heating element that vaporizes liquid introduced from said liquid channel, said a foraminous stainless steel metal mesh disposed about a portion of said vaporizing heating element within said stepped bore for maximizing the surface area for heat transfer to the cascading input liquid sample and a vapor discharge outlet port formed in said tubular body in said second segment spaced from said second end of the tubular body and intersecting with said vaporizer core.

2. The vaporizer of claim 1, wherein the tubular body is cylindrical and the first segment is an upper segment disposed above the second segment, the cylindrical body further comprising:

a second liquid sample port connected to said liquid passage formed integrally in the first segment, where said second liquid sample port provides for liquid discharge; and a thermal insulator disposed within the gap.

3. The vaporizer of claim 2, wherein the generally non-parallel surface of the gap is tapered flat and planar, and the liquid sample port and the second liquid sample port are orthogonally disposed relative to the other.

4. The vaporizer of claim 3, wherein the liquid sample port is disposed along an axis of the cylindrical body.

5. A vaporizer device for vaporizing a multi component hydrocarbon containing liquid mixture, comprising:

a body;

one or more ports configured to receive a liquid sample through the body;

a channel configured to receive the liquid sample from the one or more ports;

a recessed tapered thermal isolation gap formed on an exterior of the body and radially surrounding the channel, the recessed tapered thermal isolation gap being configured to receive and retain a thermal insulator;

a heating assembly configured to vaporize the liquid sample exiting the channel, the heating assembly being affixed within the body where at least portion of said heating assembly includes a foraminous wire mesh thereabout for efficient heat energy transfer to the liquid sample; and an outlet configured to output a vaporized liquid sample.

6. The device as claimed in claim 5, wherein the recessed tapered thermal isolation gap tapers inwardly toward the channel.

7. The device as claimed in claim 5, further comprising:

a liquid flow control element configured to intersect the channel to control a flow of the liquid sample entering the channel.

8. The device as claimed in claim 5, wherein the heating assembly is affixed within a vaporizer core, the vaporizer core being an opening formed within the body and having a radial and axial length larger than the heating assembly thereby creating a liquid flow path from the channel to an area between the outer surface of the heating assembly and the inner surface of the body and to the outlet.

9. The device as claimed in claim 5, wherein the recessed tapered thermal isolation gap is filled with an insulative material.

10. The device as claimed in claim 9, wherein the insulative material is from at least one of alumina silicate, calcium silicate, or foamed ceramics.

11. The device as claimed in claim 5, wherein the heating assembly includes a heating element and a metal housing enclosing the heating element.

12. The device as claimed in claim 11, wherein the heating element is enclosed within a metal sheath.

13. The device as claimed in claim 12, wherein the metal housing is at least partially enclosed by a metal mesh composed of stainless steel in the form of alternating bends.

14. The device as claimed in claim 5, wherein the heating assembly includes a temperature sensor therein configured to align with the outlet port of the vaporizer device, the temperature sensor providing a temperature of the vaporized liquid sample at the outlet port.

15. The device as claimed in claim 14, wherein the temperature sensor is affixed within a thermowell interior and parallel to an axial length of the heater assembly.

16. The device as claimed in claim 14, wherein the temperature sensor is affixed within a thermowell formed at an angle within a protrusion from the heater assembly.

* * * * *